United States Patent [19]

Ratz nee Simonek et al.

[11] Patent Number: 4,883,907
[45] Date of Patent: Nov. 28, 1989

[54] CARBAZATES

[75] Inventors: Ildiko Ratz nee Simonek; Pal Benko; Edit Berenyi nee Foldermann; Karoly Magyar, all of Budapest, Hungary

[73] Assignee: Egis Gyogyszergyar, Budapest, Hungary

[21] Appl. No.: 179,595

[22] Filed: Apr. 11, 1988

Related U.S. Application Data

[63] Continuation-in-part of Ser. No. 808,352, Dec. 11, 1985, Pat. No. 4,824,670.

[30] Foreign Application Priority Data

Dec. 12, 1984 [HU] Hungary ............... 4616

[51] Int. Cl.$^4$ ......................... C07C 125/063
[52] U.S. Cl. ....................... 560/24; 560/28; 560/115; 560/159; 548/371; 548/372; 549/480; 549/487
[58] Field of Search ............ 560/24, 28, 115, 159; 548/371, 372; 549/480, 487

[56] References Cited

U.S. PATENT DOCUMENTS 4,401,675  8/1983  Gartaschelli et al. ............... 560/24

FOREIGN PATENT DOCUMENTS 3665  10/1963  France ........................... 560/159
240008  10/1986  German Democratic Rep. ... 560/24
243493  3/1987  German Democratic Rep. ... 560/24

*Primary Examiner*—Bruce Gray
*Attorney, Agent, or Firm*—Herbert Dubno; Jonathan Myers

[57] ABSTRACT

The present invention relates to new carbazates of the formula (I)

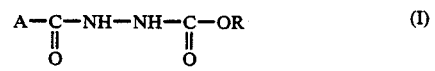

wherein
A is $C_3$ to $C_{10}$ alkenyl, $C_2$ to $C_{10}$ haloalkyl, trifluoromethyl, phenyl-$C_1$ to $C_3$ alkyl, phenyl-$C_2$ to $C_3$ alkenyl, naphthyl-$C_1$ to $C_3$ alkyl, $C_3$ to $C_7$ cycloalkyl-$C_1$ to $C_3$ alkyl, furyl which can be nitro-substituted, diphenyl-hydroxymethyl or indazolyl which can be substituted by one or more $C_1$ to $C_4$ alkoxy groups; and
R is $C_1$ to $C_4$ alkyl, and acid addition salts thereof, a process for the preparation thereof and feed additives comprising the same.

The compounds of formula (I) may be used in animal husbandry due to their weight-gain increasing and fodder utilization improving effect.

5 Claims, No Drawings

CARBAZATES

CROSS REFERENCE TO RELATED APPLICATIONS

This application is a continuation-in-part of copending Ser. No. 808,352, filed Dec. 11, 1985 now U.S. Pat. No. 4,824,670.

This invention relates to new carbazates, a process for the preparation thereof, feed-additives and ready-for-use fodders comprising the same and a method for increasing weight-gain and improving fodder-utilization of domestic animals.

In DOS #1,818,020 ethyl 2,2-dimethyl-propionyl-carbazate is disclosed but there is no reference to any weight-gain increasing effect of said compound.

According to an aspect of the present invention, there are provided new carbazates of the Formula (I),

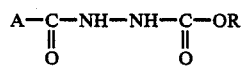
(I)

wherein
A is $C_{3-10}$ alkyl, $C_{3-10}$ alkenyl, $C_{2-10}$ haloalkyl, trifluoromethyl, phenyl-$C_{1-3}$ alkyl, phenyl-$C_{2-3}$-alkenyl, naphthyl-$C_{1-3}$ alkyl; phenyl optionally substituted by one or more identical or different substituent(s) selected from $C_{1-4}$ alkyl, halogen, $C_{1-4}$ alkoxy and hydroxy; $C_{3-7}$ cycloalkyl-$C_{1-3}$ alkyl; optionally nitro-substituted furyl; diphenyl-hydroxy-methyl or indazolyl optionally substituted by one or more $C_{1-4}$alkoxy group(s); and
R represents $C_{1-4}$ alkyl,
with the proviso that if R stands for ethyl, A is other than tertiary butyl,
and acid addition salts thereof,
R stands preferably for methyl.

In a preferred compound group of the Formula (I) A stands for phenyl-$C_{1-3}$alkyl.

The term "alkyl" used throughout the specification relates to straight or branched chained saturated aliphatic groups having the given number of carbon atoms, e.g. n-propyl, n-butyl, tert.-butyl, n-hexyl, etc. The term "alkoxy" relates to straight or branched chained alkylether groups containing the given number of carbon atoms, e.g. methoxy, ethoxy, isopropoxy, etc. The "phenyl-$C_{1-3}$alkyl" group may preferably be benzyl or β-phenylethyl, while the "phenyl-$C_{2-3}$alkenyl group may preferably be 2-phenyl-vinyl. As preferred representatives of the "$C_{2-10}$haloalky group" e.g. the 2-chloroethyl, 2-bromoethyl and 3-chloropropyl groups may be mentioned. The term "halogen" encompasses the fluorine, bromine, chlorine and iodine atoms.

The phenyl group may optionally bear one or more identical or different substituents e.g. 2-chloro-, 3,-chloro, 4-chloro, 2-bromo-, 3-iodo-, 2-hydroxy-, 3-hydroxy-, 4-hydroxy-, and 3,4,5-trimethoxyphenyl, etc., may be mentioned. The "$C_{3-7}$cycloalkyl-$C_{1-3}$alkyl group" may preferably be cyclohexylethyl.

The acid addition salts of the compounds of the Formula (I) may be formed with biologically acceptable inorganic or organic acids, e.g. mineral acids (e.g. hydrochloric acid, hydrogen bromide, hydrogen iodide, sulfuric acid, etc.), or organic acids (e.g. tartaric acid, succinic acid, citric acid, lactic acid, malic acid, fumaric acid, maleic acid, p-toluene sulfonic acid, etc.).

A particularly preferred representative of the compounds of the Formula (I) is the methyl 3-(β-phenylpropionyl)-carbazate.

Further preferred compounds of the Formula (I) are the following derivatives:
methyl 3-(3'-chloropropionyl)-carbazate;
methyl 3-(phenylacetyl)-carbazate;
methyl 3-(cyclohexylpropionyl)-carbazate; and
methyl 3-(1-naphthylacetyl)-carbazate.

According to a further feature of the present invention there is provided a process for the preparation of compounds of the Formula (I) and acid addition salts thereof which comprises (a) reacting an acid hydrazide of the Formula (II),

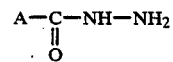
(II)

wherein A is as stated above, with a haloformiate of the Formula (III),

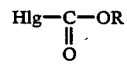
(III)

wherein Hlg stands for halogen and R is as stated above; or (b) reacting a carboxylic acid of the Formula (IV),

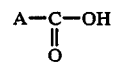
(IV)

wherein A is as stated above or a reactive derivative thereof with a carbazate of the Formula (V),

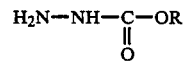
(V)

wherein R has the same meaning as stated above;

and if desired, transforming a compound of the Formula (I) into another compound of the Formula (I), and, if desired, converting a compound of the Formula (I) into an acid addition salt thereof.

According to method (a) of the process of the present invention an acid hydrazide of the Formula (II) is reacted with a haloformiate of the Formula (III). It is preferred to use a chloroformiate. The starting materials of the formulae (I) and (III) may be used in equimolar amount or the compound of the Formula (III) may be used in an excess. The reaction may preferably be accomplished in the presence of an acid binding agent. For this purpose preferably a tertiary organic base (e.g. pyridine or triethyl amine) may be used, but inorganic bases (e.g. an alkali carbonate or bicarbonate) may be applied as well. The reaction may be carried out in an inert organic solvent. As reaction medium any solvent is suitable which is capable of dissolving the starting material to the desired extent. As reaction medium preferably an ether (e.g. tetradrofuran or dioxane), acid amide (e.g. dimethyl formamide), dimethyl sulfoxide, an aromatic hydrocarbon (e.g. benzene, xylene, etc.), water, a ketone (e.g. acetone), a halogenated hydrocarbon (e.g. dichloromethane, trichloromethane, methylene chloride etc.), an alcohol (e.g. methanol, ethanol), a nitrile (e.g. acetonitrile) may be used. An excess of the starting material of the Formula (III) or the organic acid binding agent may also act as solvent.

It is particularly preferred to work in dimethyl formamide as reaction medium. The reaction may be accomplished at a temperature between 0° C. and 100° C., preferably at about 15° C.

The reaction having been completed the desired product may be isolated by known methods (e.g. evaporation and/or pouring into water) in the form of the free base or a salt.

According to method (b) of the process of the present invention a carboxylic acid of the Formula (IV) or a reactive derivative thereof is reacted with a carbazate of the Formula (V). As reactive derivative of a carboxylic acid of the Formula (IV) preferably an acid halide, ester or acid anhydride may be used. One may preferably proceed by using an acid chloride, $C_{1-4}$ alkyl ester or a mixed anhydride formed with a $C_{1-4}$ alkanoic acid. The acid chlorides have proven to be particularly advantageous.

The reaction of a chloride of an acid of the Formula (IV) and the carbazate of the Formula (V) may be carried out in the presence or absence of an acid binding agent. For acid binding agents inorganic bases (e.g. alkali metal hydroxides, carbonates or bicarbonates) or organic bases (e.g. pyridine, triethyl amine, etc.) may be used. The reaction may be accomplished in an inert solvent. As reaction medium e.g. a nitrile (e.g. acetonitrile), halogenated hydrocarbon (e.g. methylene dichloride), an aromatic hydrocarbon (e.g. benzene or toluene) or an alcohol (e.g. methanol or ethanol) may be used. On may particularly advantageously work in acetonitrile as medium. The reaction may be carried out under heating at a temperature between 40° C. and the boiling point of the reaction mixture. One may preferably work under reflux.

The reaction of an ester of a carboxylic acid of the Formula (IV) and a carbonate of the Formula (V) may be carried out advantageously in an inert solvent under heating.

The reaction of an anhydride of a carboxylic acid of the Formula (IV) and a carbazate of the Formula (V) may be carried out in an excess of the acid anhydride as medium.

The reaction of a free carboxylic acid of the Formula (V) and a carbazate of the Formula (V) may preferably be accomplished in the presence of a dehydrating agent (e.g. dicyclohexyl carbodiimide).

The compound of the Formula (I) may be isolated from the reaction mixture by known methods (e.g. crystallization on cooling, evaporation and/or pouring into water, etc.).

The above reactions (a) and (b) may be carried out by methods known per se.

A compound of the Formula (I) thus obtained may be converted into another compound of the Formula (I). Thus, a compound of the Formula (I), wherein A stands for phenyl-$C_{2-3}$alkenyl, may be reduced into the corresponding compound of the Formula (I), wherein A stands for phenyl-$C_{2-3}$alkyl. The reaction may be carried out by catalytic hydrogenation (e.g. in the presence of a palladium or platinum catalyst) or by means of a complex metal hydride (e.g. sodium hydride). The reduction may be carried out in an inert organic solvent as reduction medium.

A compound of the Formula (I) may be converted into an acid addition salt by known methods. Thus one may proceed by adding an equimolar amount or a small excess of the corresponding acid to the solution of the compound of the Formula (I) in an inert organic solvent.

The starting materials of the Formulae (II) and (III) are known (Houben-Weyl: Methoden der organischen Chemie 8, 676–680 and 101–104) and commercially available. The starting materials of the Formula (V) are also known [J. Am. Chem. Soc. 75, 2259–61 (1953)]. The starting materials of the Formula (IV) are well-known and generally available commercial products.

The compounds of the Formula (I) can be used in animal husbandry. These compounds exhibit a valuable weight-gain increasing effect accompanied by a significant fodder-utilization improving activity on domestic animals, particularly on pigs, poultry and ruminants, especially on lambs.

The weight-gain increasing effect of the compounds of the Formula (I) is shown by the following test, the results thereof being summarized in Table I. The test is carried out on lambs, the feeding period amounts to 40 days and the test compound is administered at a dose rate of 50 mg./kg. The results are the average values of three replicates. In the Table the weight-gain increase and fodder utilization values are disclosed. As test compound methyl 3-($\beta$-phenylpropionyl)-carbazate is used.

TABLE I

| Parameter | Untreated control | Compound of Example 1 |
|---|---|---|
| Average starting weight, kg. | 16.3 | 16.3 |
| Average Final weight, kg. | 27.1 | 29.5 |
| Average daily weight increase, g. | 270 | 330 |
| Average daily weight increase, related to the control, % | 100 | 122.2 |
| Average daily fodder consumption, g. | 1097 | 950 |
| Fodder utilization, kg. | 4.2 | 3.3 |
| Fodder utilization, related to the control, % | 100 | 78.6 |

The compounds of the present invention do not possess antibiotic effect and are therefore devoid of the drawbacks observed on the use of antibiotics.

The compounds of the Formula (I) have the outstanding advantage that they do not show any mutagenic effect. This is of particular importance in animal husbandry because a large number of known weight-gain promoters can be added to the fodder either not at all or but to a very limited extent because of the mutagenic effect of the said active ingredients.

It appears from the above data that the weight gain of the animals fed with a fodder comprising the compounds of the invention is significantly greater than that of the animals of the control group. At the same time the same weight gain can be achieved with a considerably smaller amount of fodder when a compound of the Formula (I) is incorporated into the animal feed. This is proof of improved fodder utilization.

According to a further feature of the invention there are provided compositions for use in animals husbandry comprising as active ingredient an amount of 0.001% to 85% by weight of a compound of the formula (I), wherein R and A are as defined above, or a biologically acceptable salt thereof in admixture with suitable inert solid or liquid carriers or diluents.

The composition of the present invention may be particularly fodder additives and fodders comprising as active ingredient an amount of 0.001 to 85% by weight of a compound of the Formula (I), wherein R and A are as defined above, or a biologically acceptable salt thereof in admixture with suitable edible solid or liquid carriers or diluents.

According to a further feature of the invention, there is provided a process for the preparation of fodder additives and fodders, which comprises admixing a compound of the Formula (I), wherein R and A are as defined above, or a biologically acceptable salt thereof with a suitable edible solid or liquid carrier or diluent and additive generally used in the production of fodder additives and fodders.

As carrier or diluent any substance of vegetable or animal origin applicable in the feeding of animals or serving as fodder can be used. For this purpose e.g. wheat, rice, maize, soybean, alfalfa, barley, cats, rye can be used in appropriate forms (grits, groats, meal, bran, etc.) furthermore fish meal, meat meal, bone meal or mixture thereof can be used as well. One may advantageously use a fiber-free green plant fodder concentrate with high protein content (e.g. VEPEX ®).

As additives e.g. silicic acid, wetting agents, antioxidents, starch, dicalcium phosphate, calcium carbonate, sorbic acid, etc. can be used. As wetting agent, e.g. nontoxic oils, preferably soybean oil, maize oil or mineral oil can be applied. Various alkylene glycols can also be used as wetting agent. The starch used may be wheat, maize or potato starch.

The fodder additives and concentrates may contain usual vitamins (e.g. vitamin A, $B_1$, $B_2$, $B_3$, $B_6$, $B_{12}$, E, K) and trace elements (e.g. Mn, Fe, Zn, Cu, J), too.

The active ingredient content of the compositions may vary within wide ranges. The fodder additives and concentrates may contain about 5–80% by weight, preferably about 10–80% by weight of the active ingredient of the Formula (I). The active ingredient content of the animal fodders ready for use may be about 1–400 ppm, preferably about 10–100 ppm.

The fodder additives and concentrates are diluted with suitable fodder components or are incorporated into suitable animal feeds to provide animal feeds ready for use.

The fodder according to the present invention can be used for the increase of weight gain and improvement of feed utilization of various domestic animals, such as pigs, lambs, cattle and poultry, particularly pigs.

Further details of the present invention are to be found in the following Examples of non-limiting character.

EXAMPLE 1

Methyl 3-(β-phenylpropionyl)-carbazate

To a solution of 164.2 g (1.0 moles) of β-phenylpropionyl hydrazide and 750 ml. of dimethyl formamide 200 ml. of pyridine are added whereupon at a temperature below 15° C. 126 g. (1.3 moles) of methyl chloroformiate are added dropwise. The reaction mixture is stirred overnight and poured into 3 l. of icecold water. The precipitated white product is filtered. Thus 145 g of the desired compound are obtained, yield 65.2%. M.p. 118° C.

EXAMPLE 2

Methyl 3-(β-phenylpropionyl)-carbazate

To a solution of 18 g. (0.2 moles) of methyl carbazate and 100 ml. of acetonitrile 33.7 g (0.2 moles) of β-phenylpropionyl chloride are added dropwise. The reaction mixture is heated to boiling for 15 hours, clarified and cooled. The crystals are filtered off. Thus 36.85 g of the desired compound are obtained, yield 80.7% m.p.: 118° C.

EXAMPLE 3

Methyl 3-(β-phenylpropionyl)-carbazate 20.0 g (0.1 moles) of methyl 3-(β-phenylpropionyl)-carbazate are dissolved in 300 ml. of methanol and the solution is hydrogenated in the presence of 0.2 g of a palladium-charcoal catalyst. The solution is evaporated. Thus 21.8 g. of the white crystalline desired compound are obtained. Yield: 98.2. M.p.: 118° C.

EXAMPLE 4

Methyl 3-(β-phenylpropionyl)-carbazate 22.0 g (0.1 mole) of methyl 3-(β-phenylacryloyl)-carbazate are dissolved in 300 ml. of methanol and the solution is hydrogenated in the presence of 0.2 g. of a palladium-charcoal catalyst. The solution is evaporated. Thus 21.8 g of the white crystalline desired compound are obtained. Yield: 98.2%. M.p.: 118° C.

EXAMPLE 5

Methyl 3-(β-phenylpropionyl)-carbazate

To a solution of 16.4 g (0.1 mole) of β-phenylpropionyl hydrazide and 75 ml. of dimethyl formamide 9.45 g. (0.1 mole) of methyl chloroformiate are added dropwise at a temperature below 15° C. The reaction mixture is allowed to stand at room temperature overnight and poured into 300 ml of icecold water. Thus 8.6 g. of the desired compound are obtained, yield 59.3%, m.p.: 118° C.

EXAMPLE 6

Methyl 3-(β-phenylacryloyl)-carbazate

To a solution of 27 g (0.3 moles) of methyl carbazate and 250 ml. of acetonitrile a solution of 50 g. (0.3 moles) of cinnamic chloride and 100 ml. of acetonitrile is added. The reaction mixture is heated to boiling for 15 hours. The mixture is cooled and the precipitated white crystals are filtered off. Thus 62.6 of the desired compound are obtained, yield 94.8%. M.p.: 165° C.

EXAMPLE 7

Methyl 3-(3'-chloro-propionyl)-carbazate

To a solution of 45 g. (0.5 moles) of methyl carbazate in 375 ml. of acetonitrile 63.5 g. (0.5 moles) of 3-chloropropionyl chloride are added dropwise. The reaction mixture is heated to boiling for 16 hours, clarified and cooled. The precipitated crystals are filtered. Thus 70.5 g. of the desired compound are obtained in the form of white crystals. Yield: 78.3%. M.p.: 129° C.

EXAMPLE 8

Methyl-3-heptanoyl-carbazate

To a solution of 69.5 g. (0.48 moles) of heptanoyl hydrazide in 160 ml. of pyridine are added. To the mixture 68.3 g. (0.72 moles) of methyl chloroformiate are added dropwise at a temperature below 15° C. The reaction mixture is stirred at room temperature for an hour and poured into 2 l. of icecold water. The precipitated crystals are filtered off. Thus 81 g. of the desired compound are obtained, yield: 83.4%. M.p.: 74°–75° C.

EXAMPLE 9

Methyl 3-(1'naphthyl-acetyl)-carbazate

To a solution of 100.1 g. (0.5 moles) of naphthyl-acetyl-hydrazide in 500 ml of dimethyl formamide 100 ml of pyridine are added. To the mixture 70.5 g (0.75 moles) of methyl chloroformiate are added and the reaction mixture is worked up according to Example 1. Thus 122.3 g. of the desired compound are obtained, yield 94.7%. M.p.: 168° C.

EXAMPLE 10

Methyl 3-(p-hydroxy-benzoyl)-carbazate 30.4 g. (0.2 moles) of p-hydroxy-benzoyl-hydrazide and 24.57 g. (0.26 moles) of methyl chloroformiate are reacted in an analogous manner to Example 1. Thus 34.4 g. of the desired compound are obtained, yield 81.9%. M.p.: 229°–230° C.

EXAMPLE 11

Methyl 3-(5'-nitro-furanoyl)-carbazate 15.7 g. (0.5 moles) of 5-nitro-furoyl-hydrazide and 11.8 g (0.125 moles) of methyl chloroformiate are reacted in an analogous manner to Example 1. Thus 16.8 g. of the desired compound are obtained, yield 73.4%. M.p.: 155° C.

EXAMPLE 12

Methyl 3-(p-chloro-benzoyl)-carbazate 36.0 g. (0.4 moles) of methyl carbazate and 70.0 g. (0.4 moles) of p-chloro-benzoyl chloride are reacted in an analogous manner to Example 2. Thus 74.5 g. of the desired compound are obtained, yield 81.5%, M.p.: 160° C.

EXAMPLE 13

Methyl 3-(3',4',5-trimethoxy-benzoyl)-carbazate 54.0 g. (0.23 moles) of 3,4,5-trimethoxy-benzoyl-hydrazide and 30 g. (0.32 moles) of methyl chloroformiate are reacted in an analogous manner to Example 1. Thus 54.25 g. of the desired compound are obtained, yield 83%. M.p.: 145° C.

EXAMPLE 14

Methyl 3-(phenylacetyl)-carbazate

To a solution of 90.1 g. (1.0 mole) of methyl carbazate and 500 ml. of acetonitrile 154.6 g. (1.0 mole) of phenyl acetyl chloride are added. The reaction mixture is heated to boiling for 15 hours and clarified. The residual oil is poured into 500 ml. of water, whereby the oil soon solidifies. Thus 158.4 g. of the white desired compound are obtained, yield 76.1%, M.p. 94°–95° C.

EXAMPLE 15

Methyl 3-benziloyl-carbazate 24.2 g. (0.1 mole) of benzilic acid hydrazide and 12.5 g. (0.13 moles) of methyl chloroformiate are reacted in an analogous manner to Example 1. Thus 22.25 g. of the desired compound are obtained, yield 74.2%. M.p.: 160°–161° C.

EXAMPLE 16

Methyl 3-(5',6'-dimethoxy-indazol-3-carbonyl)-carbazate 7.1 g (0.03 moles) of 5,6-dimethoxy-indazol-3-carbaxylic acid hydrazide and 3.7 g (0.039 moles) of methyl chloroformiate are reacted in an analogous manner to Example 1. Thus 6.21 g of the desired compound are obtained, yield 70.4%. M.p.: 235° C.

EXAMPLE 17

Methyl 3-(β-cyclohexylpropionyl)-carbazate 16.92 g (0.1 mole) of cyclohexane-propionyl-hydrazide and 12.28 g (0.13 moles) of methyl chloroformiate are reacted in an analogous manner to Example 1. Thus 18.8 g of the desired compound are obtained, yield 86%, M.p.: 113° C.

EXAMPLE 17A

Methyl 3-(p-tertiary butyl-benzoyl)-carbazate the desired compound is prepared by reacting 153.6 g. (0.8 mole) of p-tertiary butyl-benzhydrazide and 98.3 g (1.04 moles) of methyl chloroformiate in an analogous manner to Example 1. Thus 178.95 g of the desired compound are obtained, yield 89.4%, M.p.: 157°–158° C.

EXAMPLE 18

A premix for supplementing pig fodder is prepared with the following composition:

| Components | Amounts |
| --- | --- |
| Vitamin A | 3,000,000 IU |
| Vitamin $D_3$ | 600,000 IU |
| Vitamin E | 4,000 IU |
| Vitamin $K_3$ | 400 mg. |
| Vitamin $B_1$ | 600 mg. |
| Vitamin $B_2$ | 800 mg. |
| Vitamin $B_3$ | 2,000 mg. |
| Vitamin $B_6$ | 800 mg. |
| Vitamin $B_{12}$ | 10 mg. |
| Niacine | 4,000 mg. |
| Choline chloride | 60,000 mg. |
| Active agent according to Example 1 | 10,000 mg. |
| Butylhydroxytoluene (antioxidant) | 30,000 mg. |
| Flavoring substances | 8,000 mg. |
| Sodium saccharate | 30,000 mg. |
| Trace elements: | |
| Mn | 8,000 mg. |
| Fe | 30,000 mg. |
| Zn | 20,000 mg. |
| Cu | 6,000 mg. |
| I | 100 mg. |
| Twice-ground bran ad | 1,000 g. |

This premix of vitamins and trace elements is admixed with the basal fodder in a concentration of 0.5 kg. per 100 kg.

EXAMPLE 19

A premix for supplementing piglet fodder is prepared with the following composition:

| Components | Amounts |
| --- | --- |
| Vitamin A | 1,200,000 IU |
| Vitamin $D_3$ | 300,000 IU |
| Vitamin B | 2,000 IU |
| Vitamin $B_2$ | 600 mg. |
| Vitamin $B_3$ | 2,000 mg. |
| Vitamin $B_{12}$ | 5 mg. |
| Niacine | 3,000 mg. |

| Components | Amounts |
| --- | --- |
| Choline chloride | 40,000 mg. |
| Active agent according to Example 1 | 10,000 mg. |
| Butylhydroxytoluene (antioxidant) | 30,000 mg. |
| Trace elements: | |
| Mn | 6,000 mg. |
| Fe | 10,000 mg. |
| Zn | 15,000 mg. |
| Cu | 30,000 mg. |
| I | 100 mg. |
| Twice-ground bran ad | 1,000 g. |

This premix of vitamins and trace elements is admixed with the basal fodder in a concentration of 0.5 kg. per 100 kg.

EXAMPLE 20

0.5 kg. of a premix as described in Example 17 are admixed with 100.0 kg. of a basal fodder with the following composition:

| Components | Amounts, kg. |
| --- | --- |
| Maize | 37.6 |
| Barley | 25.4 |
| Wheat | 6.0 |
| Oats | 5.0 |
| Soybean | 13.0 |
| Fish Meal | 6.0 |
| Bran | 2.4 |
| Fat Powder | 1.5 |
| Premix of minerals* | 1.0 |
| Lime (fodder quality) | 1.0 |
| Sodium chloride (fodder quality) | 0.5 |
| Biolisine | 0.1 |
| Premix according to Example 17 | 0.5 |
| Total Weight | 100.0 kg. |

The active agent content of the resulting pig fodder is 50 ppm.

*The composition of the premix of minerals is as follows:

| Components | Amounts, % |
| --- | --- |
| Dicalcium phosphate | 55.0 |
| Monocalcium phosphate | 40.0 |
| Calcium carbonate | 5.0 |

EXAMPLE 21

0.5 kg. of a premix as described in Example 18 are admixed with 100.0 kg. of a basal fodder with the following composition:

| Components | Amounts, kg. |
| --- | --- |
| Maize | 25.0 |
| Wheat | 34.0 |
| Extracted soybean | 18.0 |
| Milk powder | 9.9 |
| Fish Meal | 4.0 |
| Yeast (fodder quality) | 2.0 |
| Fat Powder | 3.4 |
| Premix of minerals according to Example 19 | 1.8 |
| Lime (fodder quality) | 1.0 |
| Sodium chloride (fodder quality) | 0.4 |
| Premix according to Example 17 | 0.5 |
| Total Weight | 100.0 kg. |

The active agent content of the resulting piglet fodder is 50 ppm.

EXAMPLE 22

400 kg. of a pre-ground soybean meal are filled into a mixer, 3.1 kg. of soybean oil are added under stirring, and the mixture is stirred until the solids are coated with oil. Thereafter 9.1 kg. of an active agent according to Example 1 are added and the mixture is stirred until a homogenous blend is obtained. Finally 9.0 kg. of soybean oil are added, and the mixture is homogenized again.

EXAMPLE 23

0.5 kg. of an active agent according to Example 1 are added to 40 kg. of corn meal under stirring, and simultaneously 3.0 kg. of propylene glycol are sprayed into the mixture. Thereafter 1.4 kg. of dicalcium phosphate are added and the mixture is homogenized.

EXAMPLE 24

10 kg. of alfalfa meal and 15 kg. of VEPEX ® are stirred for 20 hours, thereafter 1 kg. of maize oil is started to spray into the mixture with an even speed so that spraying is continued during the introduction of the following additional components: 2.5 kg. of an active agent according to Example 1, 10 kg. of maize starch, 2.5 kg. of the above active agent 0.3 kg. of silicon dioxide, 0.6 kg. of ascorbic acid, 9 kg. of maize starch and 2.5 kg. of the above active agent. Thereafter the mixture is stirred for an additional 5 minutes.

EXAMPLE 25

One proceeds as described in Example 21 with the difference that butylene glycol is applied as wetting agent instead of soybean oil.

EXAMPLE 26

(A) 3.5 kg. of potato starch are admixed with 2.9 kg. of an active agent according to Example 1. 0.05 kg. of mineral oil are sprayed into the mixture, thereafter 0.2 kg. of sorbic acid, 0.4 kg. of silicon dioxide and 0.1 kg. of calcium propionate are added, and the mixture is stirred for an additional 2 minutes.

(B) 4.2 kg. of fish meal are admixed with 22 kg. of rye bran, 0.6 kg. of mineral oil are sprayed into the mixture, thereafter 4 kg. of a mixture prepared according to point (A), 10 kg. of maize meal, 4 kg. of a mixture prepared according to point (A) and 9 kg. of maize meal are introduced under stirring. Finally 0.6 kg. of mineral oil are sprayed into the mixture.

EXAMPLE 27

100 kg. of wheat bran, 10 kg. of an active agent according to Example 1, 2.5 kg. of calcium carbonate, 0.15 kg. of -tocopherol and 0.4 kg. of calcium propionate are homogenized with 4 kg. of propylene glycol.

EXAMPLE 28

10 kg. of soybean meal and 0.6 kg. of an active agent according to Example 1 are homogenized with 2.5 kg. of butylene glycol.

EXAMPLE 29

50 kg. of soybean meal, 0.6 kg. of an active agent according to Example 1, 0.5 kg. of silicon dioxide and 0.2 kg. of calcium propionate are homogenized with 1.6 kg. of soybean oil.

TABLE II

| Parameter | Untreated control | Rumensin | Example 1 | Example 6 | Example 7 | Example 17 |
|---|---|---|---|---|---|---|
| Average starting weight, kg. | 16.3 | 16.4 | 16.3 | 16.3 | 16.3 | 16.5 |
| Average final weight, kg. | 27.1 | 27.4 | 28.4 | 27.5 | 27.5 | 27.9 |
| Average daily weight increase, g. | 270 | 275 | 303 | 281 | 280 | 285 |
| related to the control, % | 100 | 102 | 112 | 104 | 104 | 106 |
| Average daily fodder consumption, g | 1097 | 1088 | 1075 | 1085 | 1082 | 1080 |
| Fodder Fertilization, kg | 4.1 | 4.0 | 3.6 | 3.9 | 3.9 | 3.8 |
| related to the control, % | 100 | 98 | 88 | 95 | 95 | 93 |

The tests are carried out on 20 lambs, the feeding period amounts to 40 days and the test compounds are administered at a dose rate of 50 mg./kg.

We claim:

1. A carbazate of the Formula (I)

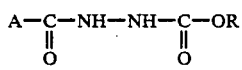

wherein

A is $C_3$ to $C_{10}$ alkenyl, $C_2$ to $C_{10}$ haloalkyl, trifluoromethyl, phenyl-$C_1$ to $C_3$ alkyl, phenyl-$C_2$ to $C_3$ alkenyl, naphthyl-$C_1$ to $C_3$ alkyl, $C_3$ to $C_7$ cycloalkyl-$C_1$ to $C_3$ alkyl, furyl which can be nitro-substituted, diphenyl-hydroxymethyl or indazolyl which can be substituted by one or more $C_1$ to $C_4$ alkoxy groups; and R is $C_1$ to $C_4$ alkyl;

or an agriculturally acceptable acid addition salt thereof.

2. The compound of the Formula (I) defined in claim 1 wherein R is methyl or an agriculturally acceptable acid addition salt thereof.

3. Methyl 3-(beta-phenylpropionyl)-carbazate or an agriculturally acceptable acid addition salt thereof as defined in claim 1.

4. Methyl 3-(3'-chloro-propionyl)-carbazate, or an agriculturally acceptable acid addition salt thereof as defined in claim 1.

5. Methyl 3-heptenoyl-carbazate, or an agriculturally acceptable acid addition salt thereof as defined in claim 1.

* * * * *